(12) United States Patent
Holstein

(10) Patent No.: US 8,302,775 B2
(45) Date of Patent: Nov. 6, 2012

(54) RAPID DEPLOYMENT FIRST AID KIT AND SYSTEM FOR REFILLING

(75) Inventor: Michael Holstein, Clearwater, FL (US)

(73) Assignee: Genuine First Aid International Ltd., Road Town (VG)

( * ) Notice: Subject to any disclaimer, the term of this patent is extended or adjusted under 35 U.S.C. 154(b) by 0 days.

(21) Appl. No.: 13/424,209

(22) Filed: Mar. 19, 2012

(65) Prior Publication Data

US 2012/0175284 A1    Jul. 12, 2012

Related U.S. Application Data

(63) Continuation of application No. 12/509,321, filed on Jul. 24, 2009, now Pat. No. 8,167,130.

(51) Int. Cl.
*B65D 69/00* (2006.01)

(52) U.S. Cl. ......... 206/572; 206/499; 206/570; 206/803

(58) Field of Classification Search ............... 206/223, 206/440, 459.5, 449, 499, 525, 526, 570–572, 206/803

See application file for complete search history.

(56) References Cited

U.S. PATENT DOCUMENTS

| | | | |
|---|---|---|---|
| 1,487,014 A | | 3/1924 | Davis |
| 1,564,152 A | * | 12/1925 | Thomson ............... 206/472 |
| 2,330,457 A | * | 9/1943 | Tremblett ............... 206/215 |
| 4,201,029 A | * | 5/1980 | Lerner et al. ............ 206/494 |
| 4,502,596 A | * | 3/1985 | Saetre et al. ............ 206/820 |
| 4,564,108 A | * | 1/1986 | Widlund et al. ........... 206/438 |
| 4,972,657 A | * | 11/1990 | McKee .................. 206/534 |
| 5,848,700 A | * | 12/1998 | Horn .................... 206/570 |
| 5,931,304 A | * | 8/1999 | Hammond ............... 206/570 |
| 7,624,869 B2 | | 12/2009 | Primer |
| 2002/0104774 A1 | | 8/2002 | Hammond |
| 2003/0009989 A1 | | 1/2003 | Knoerzer et al. |
| 2004/0256283 A1 | * | 12/2004 | Jasper et al. ............ 206/823 |
| 2005/0065492 A1 | | 3/2005 | Cole et al. |
| 2006/0289329 A1 | | 12/2006 | Miller |
| 2007/0131577 A1 | | 6/2007 | Call |

FOREIGN PATENT DOCUMENTS

| WO | WO-2011-011450 A2 | 1/2011 |
|---|---|---|
| WO | WO-2011-011450 A3 | 1/2011 |

OTHER PUBLICATIONS

Genuine First Aid 2009 First Aid Catalog.
Genuine First Aid 2009 Frequently Asked Questions, http://www.genuinefirstaid.com/faqs.htm.

(Continued)

*Primary Examiner* — Luan K Bui
(74) *Attorney, Agent, or Firm* — Wilson, Sonsini, Goodrich & Rosati

(57) ABSTRACT

A first aid system organized with pockets containing first aid and emergency preparedness supplies and equipment and a system for refilling. Each pocket in the kit contains supplies and equipment useful in providing initial care for a particular illness or injury and is quickly identified through textual labels and transparent elements. The pockets are connected into a strip of pockets which is folded to fit within a case. The strip of pockets is easily deployed from the case facilitating rapid and accurate identification, selection, and acquisition of items appropriate for initial care of a particular illness or injury by comprehensive visual presentation of the organizational scheme and the supplies and pieces of equipment themselves.

25 Claims, 1 Drawing Sheet

OTHER PUBLICATIONS

Press Release: Genuine First Aid Releases New Life Saving System—Easy Access Pockets dated Oct. 21, 2009, http://www.24-7pressrelease.com/press-release/genuine-first-aid-releases-new-life-saving-system-easy-access-pockets-121155.php.

PCT/US2010/042651 International Preliminary Report on Patentability and Written Opinion dated Jan. 24, 2012.
PCT/US2010/042651 Search Report and Written Opinion mailed Feb. 28, 2011.

* cited by examiner

US 8,302,775 B2

RAPID DEPLOYMENT FIRST AID KIT AND SYSTEM FOR REFILLING

CROSS REFERENCE TO RELATED APPLICATIONS

This application is a continuation of U.S. application Ser. No. 12/509,321, filed Jul. 24, 2009, U.S. Pat. No. 8,167,130, which is hereby incorporated by reference in its entirety.

BACKGROUND OF THE INVENTION

Medical emergencies pose a serious and prevalent threat to society. Emergency departments in the United States average approximately 400 visits for each 1000 people each year. According to the Centers for Disease Control and Prevention, Americans suffered 11,570 non-fatal injuries and 59 fatal injuries for each 100,000 people in 2007. Medical emergencies are often associated with natural or man-made disasters that involve temporary loss of services such as water, electricity, natural gas, and communications.

First aid is the initial care of illness or injury provided before professional medical care can be obtained in a professional medical facility. The key aims of first aid are to: preserve life, prevent further harm, and promote recovery. In the initial care of illness and injury, it is well established that a victim's life and chances for recovery are best protected when they receive care within a short period of time. The term "golden hour" is often used to represent the core principle of rapid intervention.

A first aid kit, which is a collection of supplies and equipment useful in providing first aid, can improve the ability of an initial caregiver to provide effective care. First aid kits known in the art commonly contain supplies such as bandages of various sizes and types, dressings, eye pads, gauze pads, butterfly closure strips, saline, antiseptic wipes, burn dressings, adhesive tape, and even oral and topical medications. In addition, first aid kits commonly contain equipment such as gloves, eye protection, face masks, scissors, tweezers, alcohol pads, chemical cold packs, hand sanitizer, thermometers, and blankets.

SUMMARY OF THE INVENTION

Described herein is a kit for administering first aid that includes a case that defines an interior compartment and includes a means of providing rapid access to its contents. The kit further includes a plurality of pockets that are connected into a strip of pockets. The strip of pockets is foldable to fit within the interior compartment of the case. Each pocket in the strip is optionally re-sealable and contains one or more first aid supplies and/or pieces of equipment useful in providing initial care for a particular injury or illness. Each pocket includes transparent elements allowing rapid visualization of its contents and bears a textual label indicating the type of condition its contents are useful in treating. One or more pockets bears a pictogram depicting instructions for use and one or more pockets bears a list of contents.

In some embodiments, the kit described herein includes a strip of pockets folded within the interior compartment of the case to facilitate rapid removal from the case and comprehensive visual presentation of all pockets once removed.

In further embodiments, the kit described herein includes a first aid guide that provides instructions for identification and initial care of injury and illness. In certain of these embodiments, the guide makes specific reference to first aid supplies and equipment contained in the kit.

In some embodiments, the kit described herein includes a strip of six pockets and the contents of each is respectively useful for: small cuts and burns, medium cuts and scratches, severe bleeding and burns, CPR, protection, and instruments. In other embodiments, the kit described herein includes a strip of six pockets and the contents of each is respectively useful for: emergency preparedness, small-medium cuts and burns, severe bleeding and burns, CPR, protection, and instruments.

In some embodiments, the kit described herein includes a case that is bi-fold, soft-sided, zippered, and made of water-resistant material. In other embodiments, the kit described herein includes a case that is bi-fold, hard-sided, made of plastic, and includes a carrying handle which facilitates wall mounting.

In some embodiments, the kit described herein includes emergency preparedness supplies and equipment.

Also disclosed herein is a system for refilling a first aid kit that includes a case that defines an interior compartment and includes a means of providing rapid access to its contents. The system further includes a plurality of re-sealable pockets connected into a strip of pockets. The strip of pockets is foldable to fit within the interior compartment of the case. Each pocket contains one or more first aid supplies useful in providing initial care for a particular injury or illness. The system further includes a refill kit designed for each pocket that contains a subset of the most commonly used first aid supplies useful in providing initial care for the particular injury or illness.

The terms "first aid" and "initial care" as used herein, refers to any act directed toward prevention, treatment, or management of illness or injury provided before professional medical care can be obtained in a professional medical facility. First aid includes care provided by lay people and care provided by people skilled in any healthcare art when the full compliment of tools, equipment, and facilities known to those skilled in the art are not available to them. First aid includes the initial care provided to a victim of illness or injury and subsequent care provided before professional medical care can be obtained in a professional medical facility.

The term "illness" as used herein, refers to deviation from physical, mental, or social well-being of a person or animal and includes by way of non-limiting examples, infection, disorder, or medical condition of the cardiovascular, muscular, skeletal, integumentary, digestive, endocrine, immune, nervous, reproductive, respiratory, or urinary systems. Illness further includes, by way of non-limiting examples, stroke, cerebral aneurism, aortic aneurism, difficulty breathing, respiratory arrest, myocardial infarction, angina, cardiac arrest, cardiac arrhythmia, shock, sepsis, encephalitis, and appendicitis. Illness includes emergent and non-emergent conditions that indicate care.

The term "injury" as used herein, refers to damage, harm, or trauma caused to the structure or function of the body of a person or animal either accidentally or intentionally and includes, by way of non-limiting examples, bruises, hemorrhage, contusions, wounds, cuts, scrapes, grazes, lacerations, burns, excess heat exposure, chemical exposure, excess cold exposure, fractures to bones and teeth, dislocations, concussion, brain trauma, penetrating objects, crushing, sprains, strains, ruptures, amputation, poisoning, overdose, bites, stings, blast, evisceration, choking, asphyxiation, drowning, electrocution, hernia, or surgery and other medical treatments. Injury includes emergent and non-emergent conditions that indicate care.

The term "first aid kit" as used herein, refers to any soft or hard, fixed or portable container that houses one or more supplies or pieces of equipment useful in providing first aid. The term includes kits designed for general use and those designed to facilitate initial care for a particular condition or in a particular setting. Particular conditions include, by way of non-limiting examples, myocardial infarction, cardiac arrest, difficulty breathing, respiratory arrest, sports injury, vehicle accident, and drowning. Particular settings include, by way of non-limiting examples, pools, beaches, ski areas, wilderness areas, sporting events, jails and prisons, childcare facilities, residences, garages, kitchens, restaurants, automobiles, boats, schools, and business offices.

DETAILED DESCRIPTION OF THE INVENTION

Figure 1:
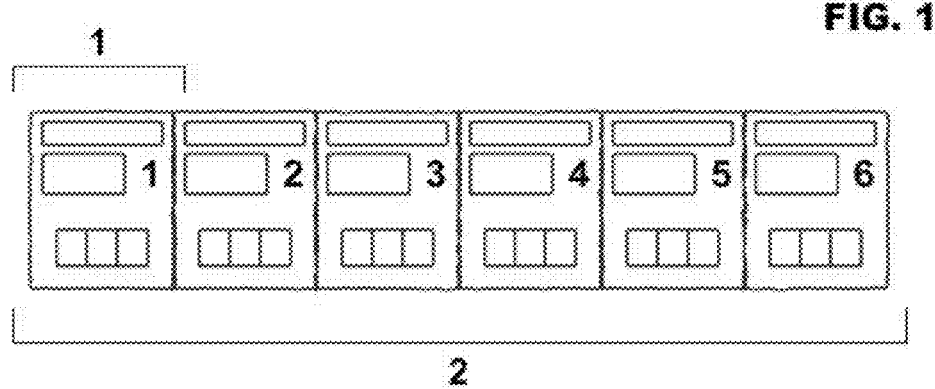
FIG. 1 shows a plurality of similarly-sized pockets 1 connected into a strip of pockets 2.

We have undertaken an analysis of prior art first aid kits. Although such kits may offer a variety of supplies and equipment, they uniformly fail to aid the initial caregiver in rapid identification, selection, and acquisition of items appropriate for initial care of a particular illness or injury. In fact, it is our contention that unorganized presentation of a multitude of first aid supplies can substantially delay initial care and result in initial care that is less likely to achieve the key aims of first aid. We have therefore identified an unrecognized need for a first aid kit that can be rapidly deployed with a simple physical action and comprehensively presents the initial caregiver with easily identified categories of first aid supplies which are easily accessible.

Thus, a primary objective of the kits described herein is to enhance the ability initial caregivers to provide rapid and effective care for illness and injury. Advantages of the kit include, but are not limited to faster visual presentation of first aid supplies and equipment, more comprehensive visual presentation of first aid supplies and equipment, and presentation of first aid supplies and equipment clearly organized into categories to provide initial care for a particular illness or injury. These advantages allow the initial caregiver to rapidly identify, select, and acquire items appropriate for initial care of a particular illness or injury.

In addition, another of the objectives of the kits described herein is to enhance the ability of caregivers to prevent harm to themselves, to victims of injury or illness, and to others in the event of a natural or man-made emergency or disaster. Illness and injury are commonly associated with these types of emergencies or disasters which involve loss of services such as water, electricity, natural gas, and communications. Advantages of the kit include, but are not limited to providing protection against airborne particulates and pathogens, temperature extremes, darkness, and being lost or cut off from communication.

Case and Strip of Pockets

Described herein are kits for administering first aid that include a case that defines an interior compartment and includes a means of providing rapid access to its contents. The case is optionally a soft pack, a hard pack, or a combination thereof. The interior of the case is optionally accessed by means of zippers, clips, hook-and-loop strips, a key/lock, a combination thereof, or the like. Rapid access to the interior of the case is preferred.

The kit further includes a plurality of similarly-sized pockets that are connected into a strip of pockets. In further embodiments, the pockets vary in size. In either of these embodiments, there are optionally two pockets, three pockets, four pockets, five pockets, six pockets, seven pockets, or eight pockets.

In some embodiments, the pockets are connected into a strip of pockets in a way that allows separation or detachment of each pocket from the strip. In further embodiments, the pockets are re-connectable.

The strip of pockets is foldable to fit within the interior compartment of the case. Each pocket in the strip is optionally re-sealable and contains one or more first aid supplies and/or pieces of equipment useful in providing initial care for a particular injury or illness. Each pocket optionally includes one or more transparent elements sufficient to allow rapid visualization of its contents and optionally bears a textual label indicating the type of condition its contents are useful in treating. One or more pockets optionally bear a pictogram depicting instructions for use and one or more pockets optionally bear a textual list of contents.

In some embodiments, the kit described herein includes a strip of pockets folded within the interior compartment of the case to facilitate rapid removal from the case and comprehensive visual presentation of all pockets once removed.

In further embodiments, the kit described herein includes a first aid guide that provides instructions for identification and initial care of injury and illness. In some embodiments, the first aid guide comprises a series of mini-guides. In other embodiments, the first aid guide is foldable in the same configuration as the strip of pockets and comprises sections that correspond to the pockets in the strip of pockets.

In some embodiments where the kit described herein includes a first aid guide, the guide makes specific reference to first aid supplies and equipment contained in the kit.

In some embodiments, the kit described herein includes a strip of six pockets and the contents of each is respectively useful for: small cuts and burns, medium cuts and scratches, severe bleeding and burns, CPR, protection, and instruments. In other embodiments, the kit described herein includes a strip of six pockets and the contents of each is respectively useful for: emergency preparedness, small-medium cuts and burns, severe bleeding and burns, CPR, protection, and instruments.

In some embodiments, the kit described herein includes a case that is bi-fold, soft-sided, zippered, and made of water-resistant material. In other embodiments, the kit described herein includes a case that is bi-fold, hard-sided, made of plastic, and includes a carrying handle which facilitates wall mounting.

In some embodiments, the kit described herein includes emergency preparedness supplies and equipment.

Strip of Pockets

In further embodiments is a plurality of similarly-sized pockets that are connected into a strip of pockets, the strip of pockets finding use, for example, in a first aid kit. In further embodiments, the pockets vary in size. In either of these embodiments, there are optionally two pockets, three pockets, four pockets, five pockets, six pockets, seven pockets, or eight pockets.

In some embodiments, the pockets are connected into a strip of pockets in a way that allows separation or detachment of each pocket from the strip. In further embodiments, the pockets are re-connectable.

The strip of pockets is foldable to fit within a case to form a first aid kit; however, such pockets optionally form a first aid kit without need for a case. In the latter instance, the strip of pockets is optionally folded and the fold held in place using a fastener. The folded and fastened strip of pockets optionally includes a means for carrying or transporting or storing the folded and fastened strip of pockets. That is the folded and fastened strip of pockets is a stand-alone first aid kit, in the absence of a carrying case.

Each pocket in the strip is optionally re-sealable and contains one or more first aid supplies and/or pieces of equipment useful in providing initial care for a particular injury or illness. Each pocket optionally includes one or more transparent elements sufficient to allow rapid visualization of its contents and bears a textual label indicating the type of condition its contents are useful in treating. One or more pockets optionally bear a pictogram depicting instructions for use and one or more pockets optionally bear a textual list of contents.

In some embodiments, the kit described herein includes a strip of pockets folded within the interior compartment of the case to facilitate rapid removal from the case and comprehensive visual presentation of all pockets once removed.

In further embodiments, the kit described herein includes a first aid guide that provides instructions for identification and initial care of injury and illness. In some embodiments, the first aid guide comprises a series of mini-guides. In other embodiments, the first aid guide is foldable in the same configuration as the strip of pockets and comprises sections that correspond to the pockets in the strip of pockets.

In some embodiments where the kit described herein includes a first aid guide, the guide makes specific reference to first aid supplies and equipment contained in the kit.

In some embodiments, the kit described herein includes a strip of six pockets and the contents of each is respectively useful for: small cuts and burns, medium cuts and scratches, severe bleeding and burns, CPR, protection, and instruments. In other embodiments, the kit described herein includes a strip of six pockets and the contents of each is respectively useful for: emergency preparedness, small-medium cuts and burns, severe bleeding and burns, CPR, protection, and instruments.

Systems for Refilling

As an additional point, it is our contention that prior art first aid kits lack an effective system to facilitate refill of spent supplies. Without such a system, prior art first aid kits may be improperly refilled and therefore unable to facilitate effective initial care when illness or injuries strike. Without such a system, prior art first aid kits may also be wastefully discarded when depleted of commonly used supplies. We have therefore identified a further unrecognized need for a system to easily and consistently refill specific contents of such a first aid kit.

Thus, another primary objective of our systems is to provide those refilling the first aid kit with a more cost-effective, more efficient, more consistent, and more accurate means of refilling spent first aid supplies and equipment. Advantages of the systems include, but are not limited to prevention of refill errors such as under-filling, over-filling, inconsistent filling, and inclusion of inappropriate items in any particular part of the kit.

Thus, also disclosed herein are systems for refilling first aid kits that includes a case that defines an interior compartment and includes a means of providing rapid access to its contents. The system further includes a plurality of re-sealable pockets connected into a strip of pockets. The strip of pockets is foldable to fit within the interior compartment of the case. Each pocket contains one or more first aid supplies useful in providing initial care for a particular injury or illness. The system further includes a refill kit designed for each pocket. In some embodiments, a refill kit contains a subset of the most commonly used first aid supplies useful in providing initial care for the particular injury or illness. In some embodiments, the refill kit contains all of the first aid supplies useful in providing initial care for the particular injury or illness.

Prior Art

Examples of prior art include U.S. Pat. Nos. 1,487,014; 5,117,981; 5,848,700; 5,931,304; 6,016,915; 6,460,702; and 6,957,738.

U.S. Pat. No. 1,487,014 discloses a first aid kit that lacks transparent elements for visualization of first aid devices. In addition, the cartons in the first aid kit are not connected to each other and are not organized to facilitate the rapid identification, selection, and acquisition of first aid devices.

U.S. Pat. No. 5,117,981 discloses a first aid kit that lacks a plurality of pockets and therefore lacks a strip of connected pockets. The kit lacks internal organization that facilitates rapid identification, selection, and acquisition of first aid devices.

U.S. Pat. No. 5,848,700 discloses a first aid kit that lacks transparent elements for visualization of first aid devices. In addition, the compartments of the kit are not organized to facilitate the rapid identification, selection, and acquisition of first aid devices. Moreover, the compartments lack pictograms depicting instructions for use and lists of contents.

U.S. Pat. Nos. 5,931,304, 6,460,702, and 6,957,738 disclose first aid kits that lack a plurality of re-sealable pockets. In addition, the packs in the first aid kits lack lists of contents and are not connected to each other in a strip.

U.S. Pat. No. 6,016,915 discloses a first aid kit that lacks re-sealable pockets. In addition, the compartments of the kit lack textual labels, pictograms depicting instructions for use, and lists of contents.

Various Non-Limiting Embodiments

Described below are various non-limiting embodiments of our first aid kits and refilling systems.

Figure 2:
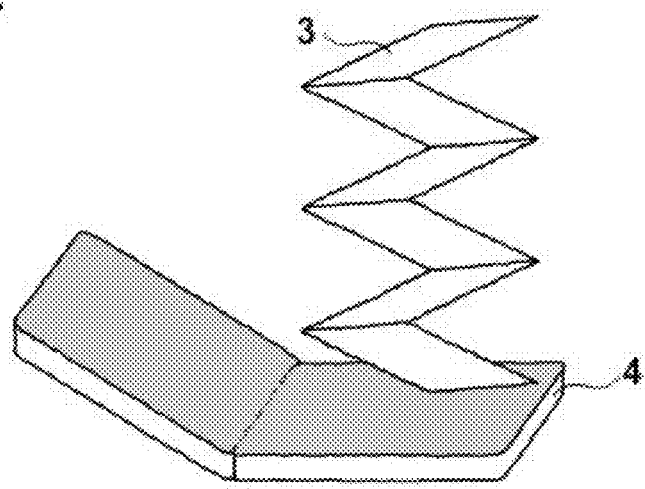
FIG. 2 shows an exploded view of a strip of pockets 3 partially folded to fit within the interior compartment of a case 4.
Figure 3:
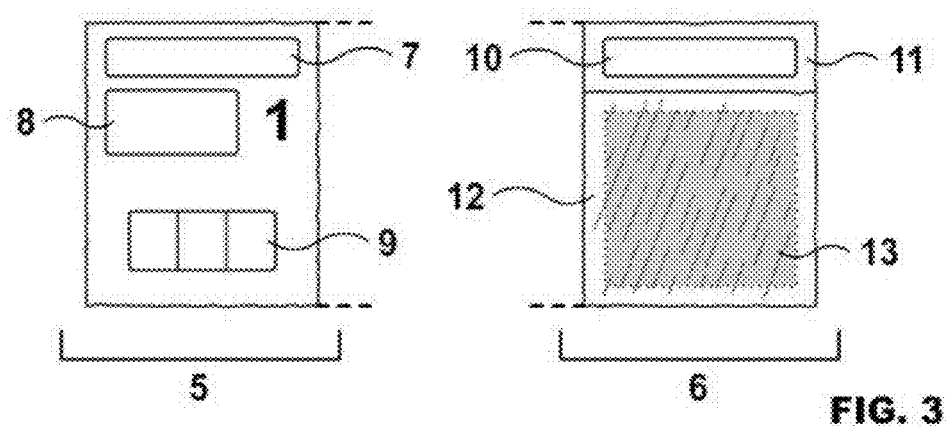
FIG. 3 shows a partial view of the front 5 and back 6 of a strip of pockets, focusing on the details of a single pocket.

Referring to FIG. 1, described herein is a kit for administering first aid that includes a case that defines an interior compartment and includes a means of providing rapid access to its contents and a plurality of similarly-sized pockets 1 connected into a strip of pockets 2. Referring to FIG. 2, the strip of pockets is foldable 3 to fit within the interior compartment of the case 4. Referring to FIG. 3, each pocket in the strip of pockets contains one or more first aid supplies 13 useful in providing initial care for a particular injury or illness. Each pocket in the strip of pockets is re-sealable and has one or more transparent elements sufficient to allow visualization of its contents 12. Each pocket in the strip of pockets bears a textual label on its front 7 and back 10 indicating the type of condition its contents are useful in treating. One or more pockets in the strip of pockets described herein bears a list of first aid supplies and equipment 8 contained therein. One or more pockets in the strip of pockets described herein bears a pictogram 9 depicting instructions for use.

In some embodiments, referring to FIG. 3, each pocket in the strip of pockets described herein bears a list of first aid supplies and equipment 8 contained therein.

In some embodiments, referring to FIG. 3, each pocket in the strip of pockets described herein bears a pictogram 9 depicting instructions for use.

An aspect of the kit described herein is a case that defines an interior compartment. A suitable case is a soft pack, a hard pack, or a combination thereof. A suitable soft pack case is made of a flexible or crushable material that is sufficiently durable and water resistant to protect the strip of pockets containing the supplies and equipment from everyday dust and moisture. Suitable materials for a soft pack case include, by way of non-limiting examples, textiles of natural fiber (e.g., cotton, wool, linen, and hemp), textiles of synthetic fiber (e.g., nylon, polyester, aramid, olefin, and acrylic), plastic (e.g., polyvinyl chloride, low-density polyethylene, and polypropylene), rubber, neoprene, silicone, and leather. Suitable materials for a hard pack case include, by way of non-limiting examples, wood, plastic (e.g., polyethylene terephthalate, high-density polyethylene, polyvinyl chloride, polypropylene, high impact polystyrene, acrylonitrile butadiene styrene, and polyamide), metal, and carbon fiber. The case includes a means of providing rapid access to its contents to facilitate rapid deployment of the strip of pockets. Means of rapid access include, by way of non-limiting examples, zippers with one slider, zippers with two sliders, hook-and-loop strips, zip-lock closures, slider zipper closures, snaps, ties, buttons, temporary adhesive, latches, clasps, and magnets.

In some embodiments, the case described herein is portable being sized and weighted to facilitate carrying or wearing. In other embodiments the case described herein is stationary or mounted to an object that is not portable including, by way of non-limiting examples, vehicles, buildings, and natural features of the earth. In some embodiments, the case described herein includes a handle that facilitates portability. In further embodiments, the handle includes holes to provide a means to mount the kit. In some embodiments, the case described herein is bi-fold, opening in two equal or unequal halves.

Referring to FIG. 1, an aspect of the kit described herein is a plurality of pockets 2. A pocket is optionally sealed on three sides and open (i.e., re-sealable) on one side forming a container. A pocket is optionally sealed on two sides and open (i.e., re-sealable) on two sides forming a container. A pocket is optionally sealed on one side and open (i.e., re-sealable) on three sides forming a container.

The pockets are connected at one or two edges via standard manufacturing techniques into a strip of pockets. In some embodiments, the pockets are oriented side-by-side such that an open side is at the top of each pocket and the top of the strip of pockets. In other embodiments, the pockets are oriented vertically in the strip of pockets. The strip of pockets is foldable, such that, when folded, it fits into the interior compartment defined by the case. Folding includes pleating by folding the strip onto itself at the connections between pockets in alternating directions and also includes, by way of non-limiting examples, rolling and bunching. To facilitate folding, the strip of pockets is made of a flexible material. Suitable flexible materials include, by way of non-limiting examples, textiles of natural fiber (e.g., cotton, wool, linen, and hemp), textiles of synthetic fiber (e.g., nylon, polyester, aramid, olefin, and acrylic), plastic (e.g., polyvinyl chloride, low-density polyethylene, and polypropylene), rubber, neoprene, silicone, and leather. The strip of pockets facilitates rapid removal of all supplies and equipment contained in the kit from the case in a simple physical motion while maintaining the organization scheme. The strip of pockets further facilitates comprehensive visual presentation of all the particular types of injury and illness for which the kit is useful in providing initial care.

In some embodiments, the pockets described herein are made of thin, flexible, transparent plastic and are folded in alternating directions at the connections between pockets to fit within the interior of the case.

In some embodiments the pockets number two, three, four, five, six, seven, or eight.

In some embodiments, the pockets are connected into a strip of pockets in a way that allows separation or detachment of each pocket from the strip. In further embodiments, the pockets are re-connectable.

Referring to FIG. 3, an aspect of the kit described herein is each pocket containing one or more first aid supplies, pieces of first aid equipment, emergency preparedness supplies, or emergency preparedness equipment known to those skilled in the art 13. First aid supplies include, by way of non-limiting examples, adhesive plastic bandages, junior adhesive plastic bandages, knuckle fabric bandages, adhesive spot bandages, fingertip fabric bandages, elbow/knee adhesive bandages, dressings, sterile eye pads, sterile eye wash, sterile saline solution, sterile gauze pads (e.g., 2×2, 3×3, and 4×4), roller gauze bandages (e.g., 3 and 4 inches wide), butterfly wound closure strips, antiseptic wipes, antiseptic towelettes, alcohol cleansing pads, povidone iodine, hydrogen peroxide, insect sting relief pads, cotton-tipped applicators, burn dressings, first aid adhesive tape, combine pads (e.g., 5×9, 8×7½ and 8×10), triangular bandages, oral medications (e.g., syrup of ipecac, antacid tablets, ibuprofen tablets, acetaminophen tablets, and chewable aspirin tablets), topical medications, and glucose paste or liquid. First aid equipment includes, by way of non-limiting examples, CPR breathing barriers, defibrillators, rescue breathing bags, compressed oxygen, face masks (e.g., paper or cloth), disposable gloves (e.g., vinyl, rubber, plastic, or nitrile, powdered or powder-free), eye protection (e.g., goggles, glasses, or eye shield), hearing protection, scissors (e.g., metal or plastic), tweezers (e.g., metal or plastic), alcohol pads, chemical cold packs, chemical heat packs, hand sanitizer, thermometers (e.g., liquid crystal strips, glass alcohol, or electronic), wooden finger splints, wire splints, and blankets (e.g., cloth, plastic, reflective metalized plastic, or Nomex®). Emergency preparedness supplies and equipment includes, by way of non-limiting examples one or more of the following: face masks (e.g., paper or cloth), eye protection (e.g., goggles, glasses, or eye shield), hearing protection, emergency blankets (e.g., cloth, plastic, reflective metalized plastic, or Nomex®), emergency ponchos (e.g., cloth, plastic, reflective metalized plastic, or Nomex®), chemical light sticks, antiseptic towelettes, triple antibiotic ointment, hand sanitizer, whistles, emergency radios, flashlights, combination radio/flashlights, batteries, water purification tablets, water purification filters, water, and human and animal food.

In some embodiments, one or more supplies or pieces of equipment are useful in providing initial care for one type of injury or illness and are contained in one pocket in the strip of pockets. In some embodiments, one or more of the supplies or pieces of equipment are useful in providing initial care for more than one particular injury or illness and are contained in more than one pocket in the strip of pockets. In some embodiments, the kit described herein contains one instance of one or more particular supplies or pieces of equipment. In some embodiments, the kit described herein contains a plurality of one or more particular supplies or pieces of equipment.

Referring to FIG. 3, an aspect of the kit described herein is a strip of pockets wherein each pocket contains one or more items appropriate for initial care of a particular type of illness or injury 13.

In some embodiments, pockets containing supplies and equipment are organized within the strip of pockets to facilitate identification, selection, and acquisition of items appropriate for initial care of a particular illness or injury. In further embodiments, the pockets are completely or partially organized from left to right within the strip of pockets in order of increasing severity of the particular illness or injury each pocket is stocked to address. In other embodiments, the pockets are completely or partially organized from left to right within the strip of pockets in order of decreasing severity of the particular illness or injury each pocket is stocked to address. In other embodiments, the pockets are completely or partially organized from left to right within the strip of pockets according to the principles of simple triage, advanced triage, or reverse triage. In other embodiments, the pockets are completely or partially organized from left to right within the strip of pockets to match the order of topics addressed in a first aid guide or published first aid standards. In still other embodiments, the pockets are completely or partially organized from left to right within the strip of pockets to facilitate identification, selection, and acquisition of items appropriate for initial care of illness or injury in a particular setting.

Referring to FIG. 3, an aspect of the kit described herein is pockets with optionally re-sealable closures 11 connected into a strip of pockets. Means of opening and re-sealing pockets include, by way of non-limiting examples, adhesive flaps, hook-and-loop strips, zip-lock closures, slider zipper closures, snaps, ties, buttons, magnets, and the like. Re-sealable closures facilitate refilling of spent supplies after care is rendered and management of supplies and equipment in multi-illness and/or multi-injury situations. Another aspect of the kit described herein is pockets with one or more optional transparent elements 12 connected into a strip of pockets. Transparent elements facilitate rapid identification, selection, and acquisition of items appropriate for initial care of a particular illness or injury by allowing the caregiver to visualize the supplies and equipment in the pocket before the pocket is opened. When pockets with transparent elements are connected into a strip of pockets the caregiver can comprehensively visualize the supplies and equipment contained in the entire kit a one glance once the folded strip is deployed from the case. Another aspect of the kit described herein is pockets with optional textual labels 7, 10 indicating the particular illness or injury the supplies and equipment therein are useful to treat connected into a strip of pockets. Textual labels include, by way of non-limiting examples, EMERGENCY PREPAREDNESS, SMALL-MEDIUM CUTS AND BURNS, SMALL CUTS AND BURNS, MEDIUM CUTS AND SCRATCHES, SEVERE BLEEDING AND BURNS, CPR, EYE, BONE, POISONING, SPRAINS, BITES AND STINGS, PROTECTION, and INSTRUMENTS.

In some embodiments, as shown in FIG. 3, the pockets connected into a strip of pockets have re-sealable plastic adhesive flaps 11 at the top of their back side. In some embodiments, the pockets connected into a strip of pockets bear textual labels 7, 10 at the top of their front 5 and back 6 sides. In further embodiments, one or more pockets connected into a strip of pockets bear a textual list 8 of supplies and equipment therein. The textual labels and lists are written in one or more languages including, by way of non-limiting examples, Mandarin, Urdu/Hindi, Spanish, English, Arabic, Portuguese, Bengali, Russian, French, Japanese, German, Telugu, Punjabi, Korean, Wu, Javanese, Tamil, Persian, Marathi, Vietnamese, and Italian. In still further embodiments, one ore more pockets connected into a strip of pockets bear one or more pictograms 9 depicting instructions for use. The pictograms are graphic symbols that represent an idea or concept and communicate meaning through pictorial resemblance to a physical object or objects.

In some embodiments, the strip of pockets described herein is folded within the interior compartment of the case to facilitate rapid removal from the case and comprehensive visual presentation of all pockets once removed. In some embodiments the strip of pockets described herein is not connected to the case and is deployed entirely free from the case. In other embodiments, the strip of pockets described herein is connected to the case and once deployed, remains attached to the case.

In some embodiments, the kit described herein includes a first aid guide that provides instructions for identification and initial care of injury and illness. The guide is written in one or more languages including, by way of non-limiting examples, Mandarin, Urdu/Hindi, Spanish, English, Arabic, Portuguese, Bengali, Russian, French, Japanese, German, Telugu, Punjabi, Korean, Wu, Javanese, Tamil, Persian, Marathi, Vietnamese, Spanish and Italian. In certain of these embodiments, the guide makes specific reference to first aid supplies and equipment contained in the kit. In further embodiments, the guide includes a symbol or icon that directs the caregiver to particular supplies contained in the kit described herein.

Also described herein is a system for refilling a first aid kit that includes a case that defines an interior compartment which includes a means of providing rapid access to its contents. Referring to FIG. 1, the system described herein also includes a plurality of similarly-sized, re-sealable pockets 1 connected into a strip of pockets 2. Referring to FIG. 2, the strip of pockets 3 is foldable to fit within the interior compartment of the case 4. Referring to FIG. 3, each pocket in the strip of pockets contains one ore more first aid supplies and/or pieces of equipment 13 useful in providing initial care for a particular injury or illness. The system also includes a refill kit designed for each pocket comprising a subset of the most commonly used first aid supplies useful in providing initial care for the particular injury or illness.

In some embodiments, one or more of the refill kits described herein contains all of the supplies and equipment that the pocket they are designed for contains prior to use. In some embodiments, one or more of the refill kits described herein contains a subset of the supplies and equipment that the pocket they are designed for contains prior to use. In further embodiments, one or more of the refill kits described herein contains the most commonly used first aid supplies useful in providing initial care for the particular injury or illness for which the corresponding pocket is designed.

EXAMPLES

The following illustrative examples are representative embodiments of the rapid deployment first aid kit and system for refilling described herein and are not meant to be limiting in any way.

Example 1

Soft-sided Rapid Deployment First Aid Kit

A case was constructed from a flexible, water-resistant textile of nylon fiber by techniques well known to the manufacturing arts. The case was bi-fold and symmetrical, consisting of two equal halves. A plastic zipper with two sliders was included to provide a means of rapid to the contents of the case. In addition, a strip of pockets was constructed from thin, flexible, transparent plastic by techniques well known to the manufacturing arts. The strip of pockets consisted of six pockets, all oriented in the same direction, each of which was sealed on three sides and open on one side forming a container. Each pocket had a flap of plastic at the top of its back side to provide a means of opening and closing the pocket. The flaps of plastic were coated with a strip of lightly-binding adhesive by techniques well known to the manufacturing arts which allowed them to be sealed and re-opened many times.

The front side of the strip of pockets, as well as the flap on the back sides of each pocket, was coated with a permanent opaque colorant by techniques well known to the manufacturing arts. This rendered the coated surfaces opaque and allowed printing of text and images.

All pockets were printed with a textual label at the top of the front side as well as on the flap of the back side which indicated the medical condition for which its planned contents were useful in providing initial care. The first pocket was labeled "SMALL CUTS AND BURNS." The second pocket was labeled "MEDIUM CUTS AND SCRATCHES." The third pocket was labeled "SEVERE BLEEDING AND BURNS." The fourth pocket was labeled "CPR BREATHING BARRIER." The fifth pocket was labeled "PROTECTION." The sixth pocket was labeled "INSTRUMENTS."

The first, second, third, fifth, and sixth pockets were printed, on the front side just below the textual label, with a list of planned contents. The first pocket listed ANTISEPTIC TOWELETTES, STERILE GAUZE PADS, ADHESIVE BANDAGES, ANTIBIOTIC OINTMENT, BURN CREAM, and COTTON TIP APPLICATORS. The second pocket listed CLEANSING WIPES, STERILE GAUZE PADS, EYE WASH 10 ML, EYE PADS, PRESSURE BANDAGES, and BUTTERFLY WOUND CLOSURES. The third pocket listed FIRST AID TAPE ROLL and BLOOD STOPPER DRESSING 10 CM×10 CM. The fifth pocket listed VINYL GLOVES, ALCOHOL CLEANSING PADS, and CHEWABLE ASPIRIN TABLETS. The sixth pocket listed ASSORTED SAFETY PINS and EMERGENCY FIRST AID GUIDE.

The first, second, third, and fourth pockets were printed, on the front side just below space for the list of contents, with a pictogram depicting instructions for use. The pictograms on the first, second, and third pockets were further labeled with text.

The pockets were filled by techniques known in the art with the first aid supplies and equipment described in the printed list for each.

The emergency first aid guide in the sixth pocket was printed by the American Red Cross according to first aid standards they endorse. The instructions in the guide include icons when first aid supplies or equipment are called for to render initial care.

The strip of six pockets was folded at the five connections between pockets in alternating directions such that the strip of pockets fit into the interior compartment of the soft-sided case.

To use the kit described in this example, an initial caregiver will first identify one or more victims of illness or injury. The initial caregiver will unzip the case and in a single motion deploy the folded strip of pockets. Once deployed, the strip will comprehensively visually inform the caregiver of the illness or injury for which each pocket is stocked to provide initial care. The caregiver will get this information via the textual labels on the front and back side of each pocket as well as via the transparent elements of the back side of each pocket which will allow the caregiver to see the individual supplies and equipment contained in each pocket. The caregiver may or may not choose to consult the emergency first aid guide. The caregiver will select one or more pockets stocked to provide initial care for the situation and after a glance at the pictogram depicting instructions for use, use the re-sealable flap on the back of the each pocket to access the supplies and equipment. The caregiver will then render initial care. If the caregiver chooses to consult the emergency first aid guide, they will be directed to particular supplies and equipment which they will identify via the comprehensive visual presentation that the strip of pockets in the kit will provide.

Example 2

Refill System for Rapid Deployment First Aid Kit

The first aid kit described in Example 1 was constructed. The system for refilling included the first aid kit and refill kits. Refill kits were constructed that were specifically designed for each of the six pockets in the strip of pockets of the first aid kit. Refill kits were constructed using techniques well known to the manufacturing arts. Each refill kit included a subset of the most commonly used supplies and/or pieces of equipment useful in providing initial care for the particular injury or illness addressed by each pocket. Each refill kit was clearly marked to indicate which pocket of the kit it was designed to refill.

Refill kits were constructed for pockets that address emergency preparedness, small cuts and burns, medium cuts and scratches, severe bleeding and burns, CPR, protection, and instruments. The refill kit for the emergency preparedness pocket contained face masks, an emergency blanket, a light stick, antiseptic towelettes, triple antibiotic cream, and hand sanitizer. The refill kit for the small cuts and burns pocket contained adhesive plastic bandages, junior plastic bandages, knuckle fabric bandages, adhesive spot bandages, fingertip fabric bandages, elbow/knee adhesive bandages, burn cream, antiseptic towelettes, antibiotic ointment, 2×2 sterile gauze pads, and cotton tipped applicators. The refill kit for the medium cuts and scratches pocket contained antiseptic towelettes, 2×2 sterile gauze pads, 3×3 sterile gauze pads, 4×4 sterile gauze pads, a roller gauze bandage, a sterile eye pad, 10 ml sterile eye wash, and butterfly wound closures. The refill kit for the severe bleeding and burns pocket contained a roll of first aid tape, a 5×9 combine pad, an 8×10 combine pad, and a roller gauze bandage. The refill kit for the CPR pocket contained a CPR breathing barrier. The refill kit for the protection pocket contained exam quality vinyl gloves, an instant cold compress alcohol cleansing pads, an insect sting relief pad an emergency blanket, chewable aspirin tablets, and a triangular bandage. The refill kit for the instruments pocket contained plastic tweezers, scissors, assorted safety pins, and finger splints.

The system for refilling a first aid kit will be used after one or more pockets of the rapid deployment first aid kit are used and one or more of the supplies or pieces of equipment spent. The caregiver, or another, will empty the contents of the appropriate refill kit into each pocket that was used. Once refilled, each pocket will be re-sealed by means of its adhesive plastic flap.

What is claimed is:
1. A first aid system comprising:
   (a) a case that defines an interior compartment and includes a means of providing rapid access to its contents;
   (b) a plurality of similarly-sized, re-sealable pockets connected into a strip of pockets, the strip of pockets being foldable to fit within the interior compartment of the case; each pocket containing one or more first aid supplies or pieces of equipment useful in providing initial care for a particular injury or illness; and
   (c) a refill kit designed for refilling each said pocket comprising first aid supplies or pieces of equipment useful in providing initial care for the particular injury or illness said refill kit indicates which pocket of the plurality of pockets it is designed to refill.

2. The first aid system of claim 1, wherein each said pocket comprises transparent elements allowing visualization of its contents and a textual label indicating the type of condition its contents are useful in treating.

3. The first aid system of claim 1, wherein one or more of said pockets comprises a pictogram depicting instructions for use.

4. The first aid system of claim 1, wherein one or more of said pockets comprises a list of contents.

5. The first aid system of claim 1, wherein at least one refill kit contains a CPR breathing barrier.

6. The first aid system of claim 1, wherein at least one refill kit contains one or more sterile dressings.

7. The first aid system of claim 1, wherein at least one refill kit contains one or more pairs of disposable gloves.

8. The first aid system of claim 1, wherein at least one refill kit contains one or more bandages.

9. The first aid system of claim 1, wherein at least one refill kit contains one or more packets of triple antibiotic ointment.

10. The first aid system of claim 1, wherein at least one refill kit contains a plurality of aspirin.

11. The first aid system of claim 1, wherein at least one refill kit contains one or more roller bandages.

12. The first aid system of claim 1, wherein at least one refill kit contains one or more sterile gauze pads.

13. The first aid system of claim 1, wherein at least one refill kit contains a triangular bandage.

14. The first aid system of claim 1, wherein at least one refill kit contains a packet of burn cream and a plurality of cotton-tipped applicators.

15. The first aid system of claim 1, wherein at least one refill kit contains a plurality of antiseptic towelettes.

16. The first aid system of claim 1, wherein at least one refill kit one or more sterile eye pads, one or more vials of sterile eye wash, and a plurality of butterfly wound closures.

17. The first aid system of claim 1, wherein at least one refill kit contains a roll of first aid tape.

18. The first aid system of claim 1, wherein at least one refill kit contains a plurality of alcohol cleansing pads.

19. The first aid system of claim 1, wherein at least one refill kit contains a plurality of safety pins.

20. The first aid system of claim 1, wherein at least one refill kit contains an emergency blanket and a cold pack.

21. The first aid system of claim 1, wherein at least one refill kit contains a pair of tweezers.

22. The first aid system of claim 1, wherein at least one refill kit contains one or more insect sting relief pads.

23. The first aid system of claim 1, wherein at least one refill kit contains a pair of scissors and a plurality of wooden finger splints.

24. The first aid system of claim 1, comprising six refill kits and the contents of each is respectively useful for:
   (a) Small Cuts and Burns;
   (b) Medium Cuts and Scratches;
   (c) Severe Bleeding and Burns;
   (d) CPR;
   (e) Protection; and
   (f) Instruments.

25. The first aid system of claim 1, comprising six refill kits and the contents of each is respectively useful for:
   (a) Emergency Preparedness;
   (b) Small-Medium Cuts and Burns;
   (c) Severe Bleeding and Burns;
   (d) CPR;
   (e) Protection; and
   (f) Instruments.

* * * * *